United States Patent [19]

Richmond et al.

[11] Patent Number: 4,826,494
[45] Date of Patent: May 2, 1989

[54] VACUUM WOUND DRAINAGE SYSTEM

[75] Inventors: James W. Richmond, Kalamazoo; Robert G. Tice, Portage; William M. Booth, III, Paw Paw, all of Mich.

[73] Assignee: Stryker Corporation, Kalamazoo, Mich.

[21] Appl. No.: 18,894

[22] Filed: Feb. 25, 1987

Related U.S. Application Data

[62] Division of Ser. No. 670,177, Nov. 9, 1984, Pat. No. 4,655,754.

[51] Int. Cl.⁴ .............................................. A61M 1/00
[52] U.S. Cl. .................................... 604/323; 604/126
[58] Field of Search ............... 604/317, 319, 320, 321, 604/323, 333

[56] References Cited

U.S. PATENT DOCUMENTS

| Re. 29,321 | 12/1975 | Holbrook | 215/309 |
| 3,719,197 | 3/1971 | Pannier | 137/205 |
| 3,768,478 | 8/1972 | Fertik | 128/276 |
| 3,982,538 | 7/1974 | Sharpe | 128/276 |
| 4,073,294 | 7/1975 | Stanley | 128/278 |
| 4,178,932 | 9/1977 | Ryder | 128/276 |
| 4,306,558 | 2/1980 | Kurtz | 128/276 |
| 4,443,220 | 3/1982 | Houer | 604/408 |
| 4,465,485 | 5/1983 | Kashmer | 604/320 |
| 4,569,674 | 8/1982 | Phillips | 604/119 |

Primary Examiner—Edward M. Coven
Attorney, Agent, or Firm—Flynn, Thiel, Boutell & Tanis

[57] ABSTRACT

Apparatus for selectively blocking passage of lipids in a liquid flow path. A baffle interposed in the liquid flow path is of nonpolar material and is arranged to permit liquid flow therethrough with contact of said liquid with the nonpolar material of the baffle for removing lipids from the flow. In one embodiment, the baffle is interposed between the wound drain connection and vacuum connection in a drain reservoir and protects the hydrophobic filter which is at the end of the vacuum passage communicating with the interior of the drain reservoir bottle. The baffle enables use of a nonpolar material for the hydrophobic filter and avoids coating and thereby clogging of the hydrophobic filter by lipids in the liquid drained from a wound.

12 Claims, 4 Drawing Sheets

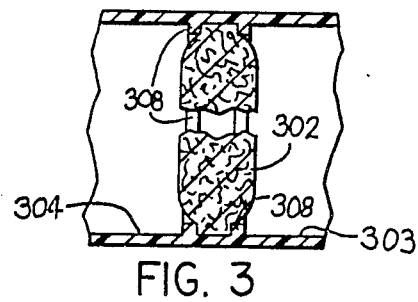
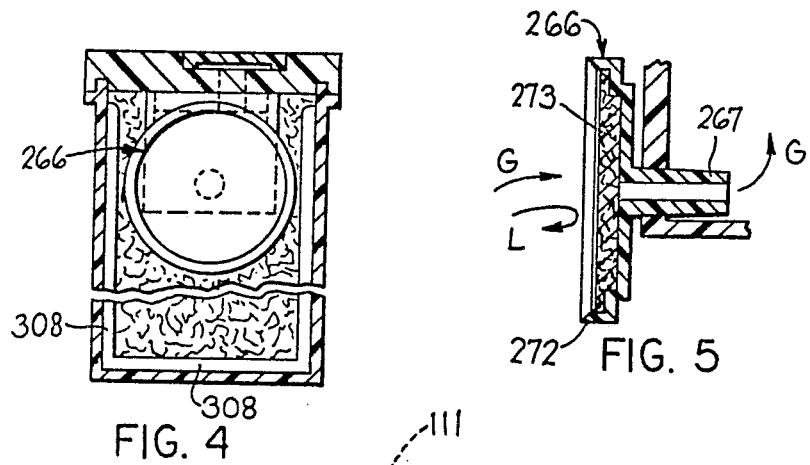
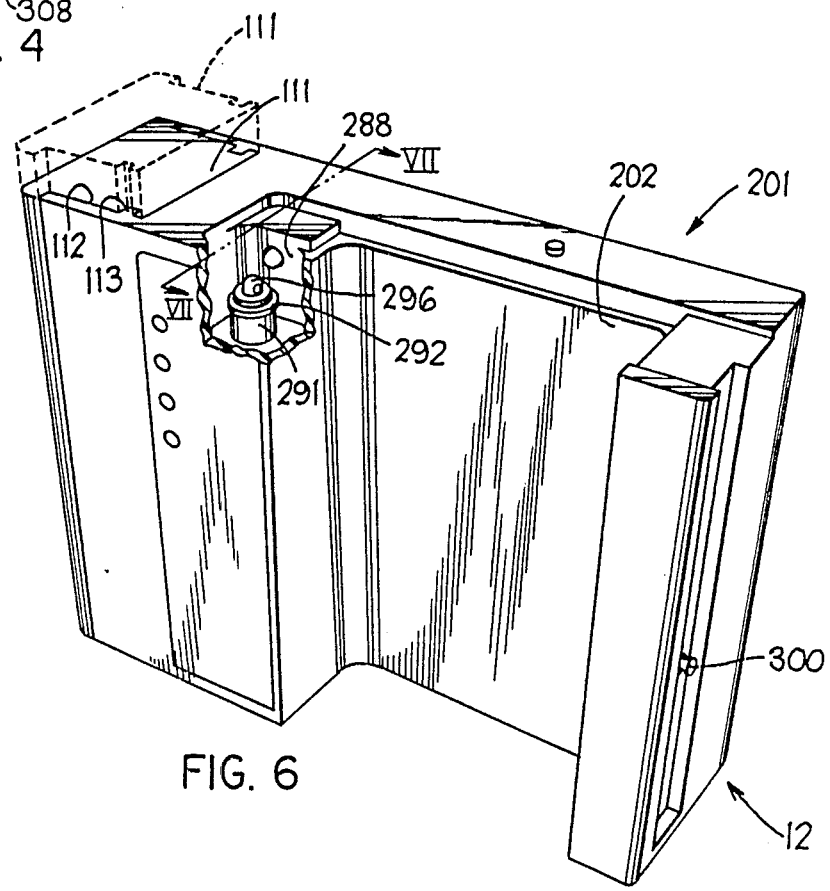

VACUUM WOUND DRAINAGE SYSTEM

This is a division of application Ser. No. 670,177 filed Nov. 9, 1984, now U.S. Pat. No. 4,655,754.

FIELD OF THE INVENTION

This invention relates to a vacuum drainage system for wounds, and more particularly to such a system having a reservoir connectable to the wound for receiving drainage liquid therefrom and apparatus for applying a subatmospheric pressure to the reservoir.

BACKGROUND OF THE INVENTION

U.S. patent application Ser. No. 404,791, now U.S. Pat. No. 4,569,674 issued Feb. 11, 1986, assigned to the assignee of the present invention, discloses a wound vacuum drainage system of the above mentioned kind.

While the latter has been found satisfactory in operation, Applicants have been engaged in a continuing effort to improve on systems of this type. Applicants have determined that by installing a hydrophobic filter in the drain reservoir, between the liquid chamber thereof and the vacuum passage, the apparatus of the prior application can be simplified, for example by elimination of a float valve, while protecting the vacuum passage in the drain reservoir and the vacuum pump in the base unit against contamination by wound drainage liquid from the drain reservoir.

However, Applicants have also found that wound drainage liquid often includes lipids (fatty substances) which tend to coat and hence clog the hydrophobic filter and that this may interfere with evacuating the drain reservoir to the desired subatmospheric pressure level, to enable continued vacuum draining of the wound.

Accordingly, the objects and purposes of this invention include provision of:

Apparatus for suction draining of a wound in which a hydrophobic filter is interposed in the connection between the reservoir chamber and the vacuum line to which the suction pump of a base unit are connectable, for preventing contamination of such vacuum passage and suction pump with wound drainage liquid.

An apparatus as aforesaid in which coating and hence clogging of the hydrophobic filter by lipids in the wound drainage liquid is prevented or avoided to increase the useful life span of the drain reservoir by making it possible to repeatedly charge same with vacuum by connection to a base unit.

An apparatus as aforesaid in which protection of the hydrophobic filter is provided at relatively low cost in a relatively simple manner.

Other objects and purposes of the invention will be apparent to persons of ordinary skill in this art by reading the accompanying specification and inspecting the accompanying drawings.

BRIEF DESCRIPTION OF THE DRAWINGS

FIG. 3 is an enlarged fragmentary cross-sectional view taken substantially on the line III—III of FIG. 2.

FIG. 4 is a fragmental sectional view substantially taken on the line IV—IV of FIG. 2.

FIG. 5 is a central cross-sectional view substantially taken on the line V—V of the hydrophobic filter unit of FIG. 4.

FIG. 6 is a pictorial, partially broken view of a base unit for receiving the drain reservoir of FIG. 1.

DETAILED DESCRIPTION

Figure 1:
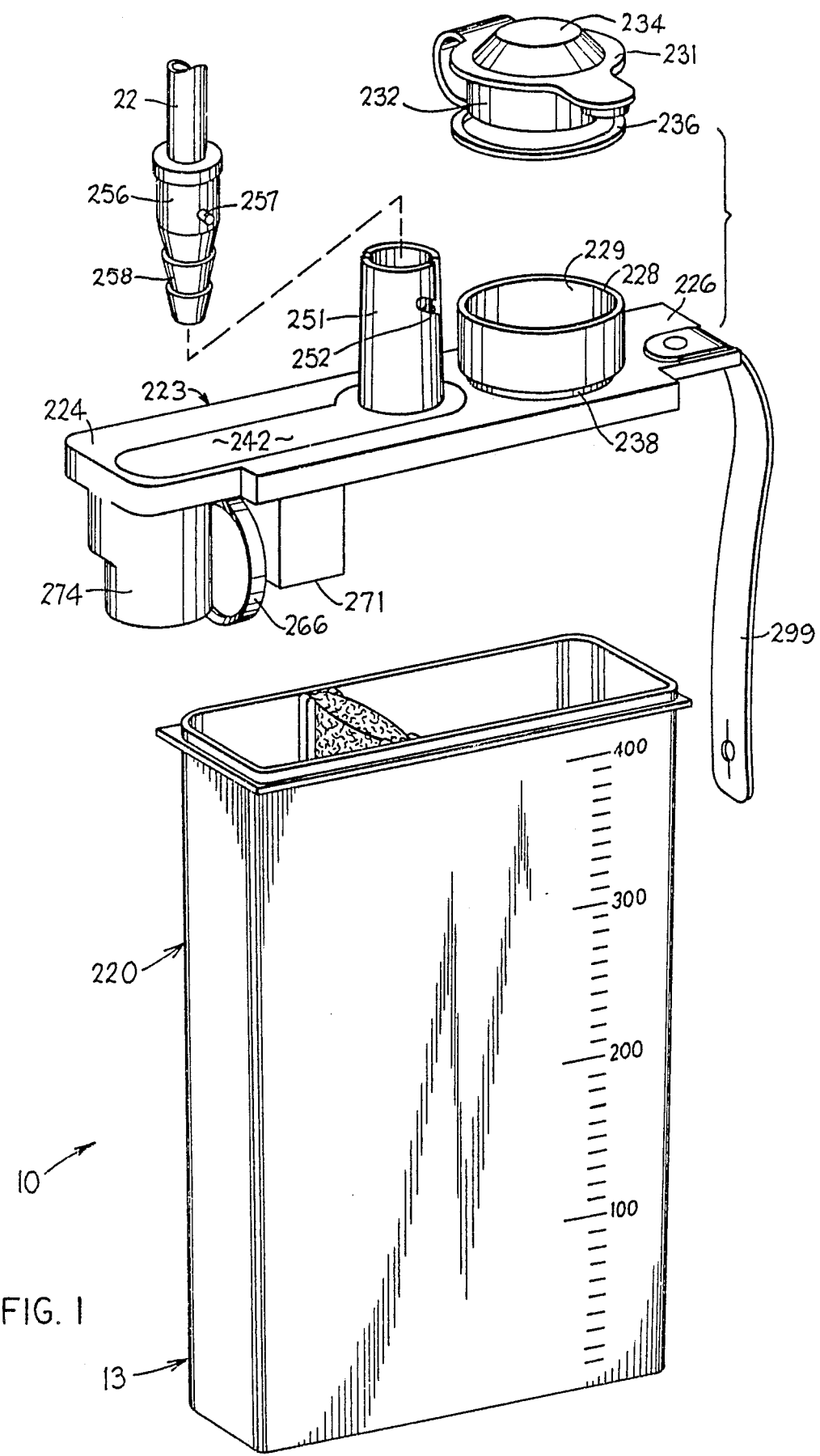
FIG. 1 is an exploded pictorial view of a drain reservoir embodying the invention.
Figure 2:
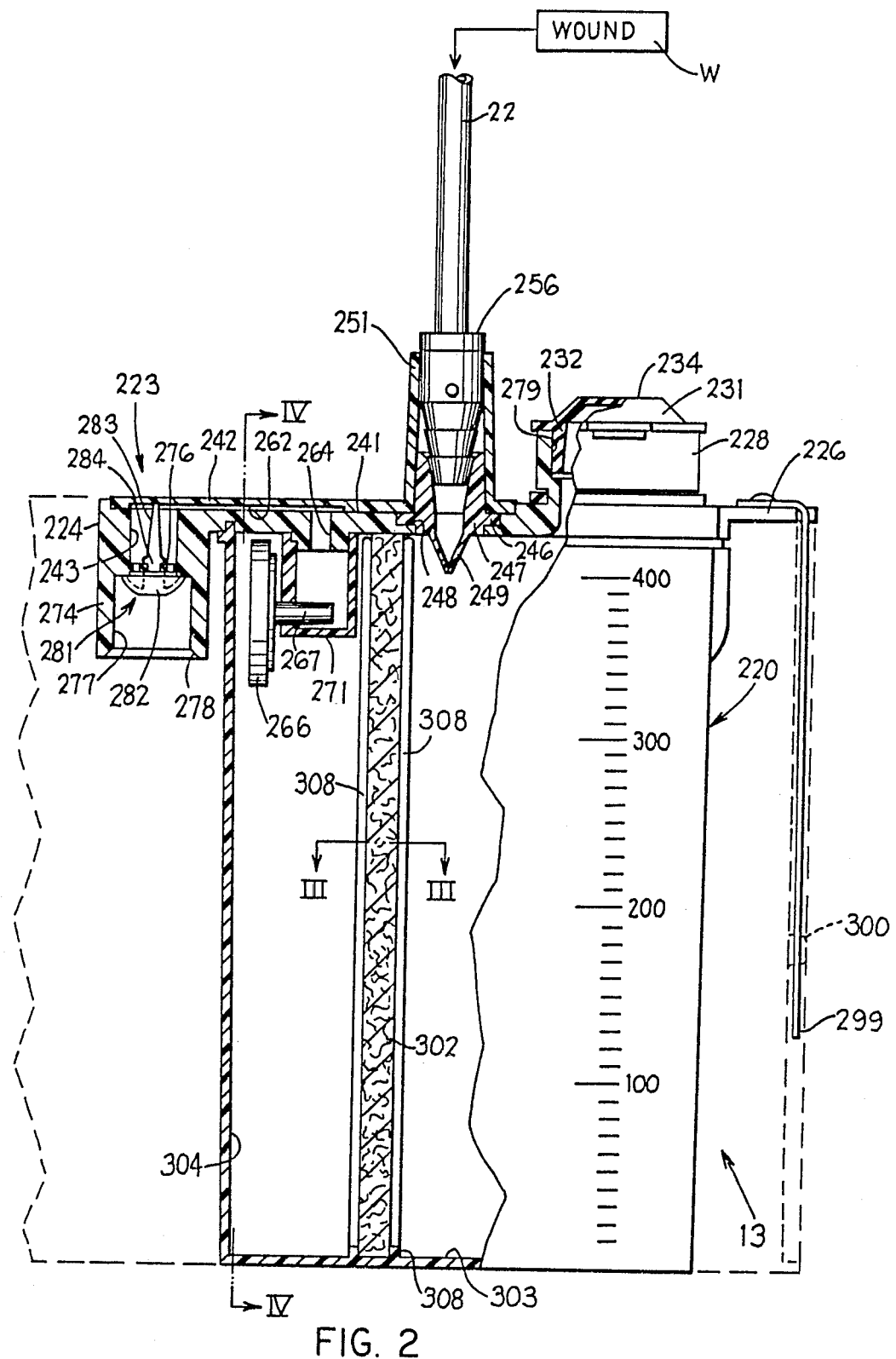
FIG. 2 is a partially broken front view of the drain reservoir of FIG. 1.

A continuous vacuum drainage system 10, for draining a closed wound, includes a base unit 12 (FIG. 6) and a drain reservoir 13 (FIGS. 1 and 2). The drain reservoir is releasably securable to the base unit for partial evacuation to a subatmospheric (negative) pressure. A wound drain tube 22 is used to connect the reservoir 13 to a patient's wound W to be vacuum drained. The reservoir 13 is disconnectable from the base unit 12 without impairing the negative pressure within the reservoir 13. Thus, the reservoir 13 can be used for vacuum wound drainage both while connected to the base unit 12, as well as after disconnection from the base unit, thus permitting the reservoir to be carried by the patient or on a mobile patient support (not shown) to locations remote from the base unit 12.

Figure 7:
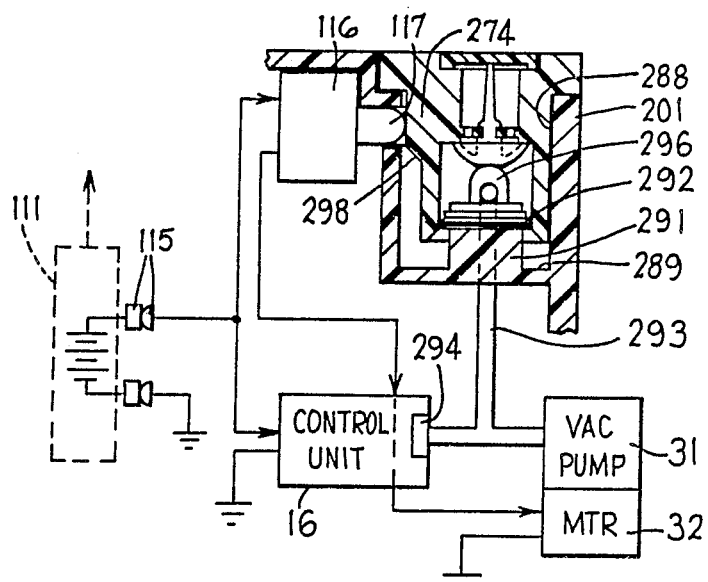
FIG. 7 is a fragmentary cross-sectional view substantially taken on the line VII—VII of FIG. 6.

The base unit 12, in the embodiment shown in FIGS. 6 and 7, comprises a housing 201 having a forwardly facing groove 202 into which the reservoir 13 is downwardly insertable. As schematically indicated in FIG. 7, the housing 201 contains a control unit 16, which may be of the type shown in prior U.S. application Ser. No. 404,791 assigned to the assignee of the present invention, which control unit 16 is enabled by actuation of a power switch 116 to energize the motor 32 of a vacuum pump 31 from an electric power source such as a battery pack 111. The mentioned elements 16, 31, 32, 111 and 116 preferably operate substantially in the manner described in aforementioned application Ser. No. 404,791, such that with the actuator 117 of switch 116 actuated by insertion of a receptacle 113 into the recess 202 in the housing 201 of the base unit 12, the control unit 16 will sense the level of vacuum in the drain reservoir 13 (by means of a conventional vacuum transducer 294) and, if an insufficient vacuum level exists, will cause the pump 31 to run for a sufficient time as to reduce the pressure in the drain reservoir 13 to a desired subatmospheric level.

In the embodiment shown, the battery pack 111 is arranged as a unit vertically slidable into and removable from a recess 112 in the left (FIG. 6) end of the housing 201 in which it is vertically guided by tongue-in-groove means 113. As schematically indicated in FIG. 7, electrical contact between the battery pack 111 and electrical apparatus within the housing 201, including switch 116 and control unit 16, is established, with the battery pack 111 installed in the housing as indicated in solid lines in FIG. 6, by means of opposed relatively vertically movable conductive contacts 115.

The drain reservoir 13 (FIGS. 1 and 2) comprises a hollow, substantially rectangular, upward opening bottle 220, the top of which is closed by a fixed cover 223. The left and right ends 224 and 226 of the cover 223 overhang the sides of the bottle 220. An emptying spout 228 fixedly upstands from the cover 223 above the rightward portion of the bottle 220 and has a through opening 229 for emptying liquid from the bottle. A resilient cap 231 is positionable atop the spout 228 and has a skirt 232 snugly received in the through opening 229 for sealing the spout against air leakage therepast into the bottle 220. In the embodiment shown, the top 234 of the cap 231 resiliently flexes to a concave shape, when the bottle is at a subatmospheric pressure, to visually indicate that a subatmospheric pressure condition exists in the bottle. A retaining ring 236 fixed to the cap 231 fits in an undercut 238 in the spout 228 to prevent loss of the cap 231 when it is removed from the spout for pouring liquid from the bottle.

An upward opening recess 241 extends from the central portion of cover 223 nearly to the left end thereof. A platelike closure 242 is sealingly fixed in the recess 241 to hold the radially protruding flange 246 of a tubular resilient valve member 247 in a sub-recess 248 of the cover 223. At the lower end of the tubular valve member 247 is a one-way, or check, valve, here of the so-called "duck bill" type, which permits fluid flow into, but not out of, the bottle 220. The platelike closure 242 has an upstanding chimney 251 closely surrounding the tubular valve member 247 and extending upward therebeyond. The chimney 251 has diametrally opposed, substantially J-shaped, bayonet locking slots 252. The resilient member 247 and chimney 251 form a socket compatible with a conventional connector plug 256 on the outlet end of the wound drain tube 22. The connector plug 256 has diametrally extending bayonet pins 257 coactive with the J-shaped locking slots 252 to releasably hold the plug 256 in the chimney 251 with the tapered, frustoconically ridged bottom 258 of the plug snugly fitted in sealed relation in the upper portion of the tubular valve member 247 in spaced relation above the duck bill valve 249.

A vacuum passage is formed by a leftwardly-rightwardly extending recess 262 in the underside of the platelike closure 242 to the left of the chimney 251 and vertical holes 263 and 264 extending downward from the ends of such recess 262 in the overhanging left end portion 224 of the cover 223 and in the portion of the cover 223 in the leftward portion of the bottle 220.

A commercially available, disklike, microporous hydrophobic filter unit 266 (FIGS. 2, 4 and 5) is disposed in the upper leftward portion of the bottle 220 and has a rightwardly protruding hollow outlet stem 267 communicating, here through a hollow adapter 271, with the hole 264. In the embodiment shown, the microporous hydrophobic filter unit 266 comprises a disklike, undercut surround 272 from which said stem 267 extends and which contains a 0.2 micron polytetrafluoroethylene (PTFE, or as known by the mark Teflon) screen 273, comprising material known as Goretex 111177, backed by polypropylene, which filter unit is available from Filtertek, Inc. of Hebron, Ill. The hydrophobic filter unit 266 is capable of passing gases therethrough (as indicated by the arrows G in FIG. 5) but not liquid (as indicated by the arrow L).

At the left end of the vacuum passage (formed by recess 262 and holes 263 and 264, 262, 263 FIG. 2), the hole 263 extends part way down into a leg 274 integrally depending from the left end of the cover 226, near the left side of the bottle 220. Approximately midway down the leg 274, a wall 276 extends diametrally and forms a bottom to the hole 263, separating same from a larger diameter downwardly opening recess 277 terminating at its lower end in a vacuum port 278.

A check, or one-way, valve 281 here comprises a resilient umbrella valve head 282 from which a resilient coaxial stem 283 extends upward through a central opening in the wall 276, the stem being enlarged adjacent its lower end at 284 immediately above the wall 276 to firmly hold the radially enlarged head 282 in sealing contact against the upper end wall of the recess 277. Holes through the peripheral portion of the wall 276 are thus normally closed by the umbrella valve head 282 which radially overlaps same when the air pressure in the recess 277 is higher than that in the hole 263, i.e., when there is a subatmospheric pressure in the bottle 220. On the other hand, the valve head 282 is capable of deflecting downward at its periphery in response to a drop in pressure in the recess 277 to below the pressure in the bottle 220, so as to draw air from the bottle through the hydrophobic filter 266, passage 264, 262, 263 and then down through the recess 277.

In the embodiment shown, the base unit housing 201 has a recess 288 (FIGS. 6 and 7) which opens upward immediately to the left of the bottle receiving groove 202. The recess 288 is sized to receive downward thereinto, in clearance relation, the depending leg 274 of the bottle cover 223. Projecting upward through the floor 289 of the recess 288 is a hollow cylindrical fitting 291 on which is coaxially fixed a resilient annular seal 292. The fitting 291 is hollow and connected to the vacuum pump 31 by a vacuum line 293 which also connects to a conventional vacuum transducer 294 in the control unit 16, so that the control unit 16 can be influenced by the level of subatmospheric pressure in the line 293. The fitting 291 has a perforated head 296.

With the bottle 220 received in the forward opening groove 202 and the depending leg 274 downwardly received in the recess 288 as in FIG. 7, the vacuum port 278 is sealed by the annular seal 292 to effect an air-tight vacuum connection between the vacuum pump 31 and the recess 277 in the drain reservoir cover 223. Operation of the vacuum pump 231 reduces the gas pressure in the recess 277 and when the latter is at a level below the gas pressure within the bottle 220, the periphery of the umbrella valve head 282 is pulled downward by such pressure differential to open communication between the recess 277 and the passage 263, 262, 264 and hence through the hydrophobic filter 266 to the interior of the bottle 220 to lower the pressure in the bottle to a desired subatmospheric pressure. Such connection of the vacuum pump 31 to the bottle 220 is normally carried out after the tube 22 has been emplaced in a closed wound W.

In the embodiment shown in FIGS. 6 and 7, the vacuum pump 31 is enabled by depression of the switch actuator 117 by contact with the side of the leg 274 as the drain receptacle 13 is being downwardly received in the base unit 12 (with bottle 220 in forward facing groove 202 and leg 274 received in the upward opening recess 288). In the preferred embodiment shown, the switch actuator 117 also acts as a mechanical aid to help prevent unintended movement of the drain receptacle 13 out of its vacuum charging position in the base unit 12 shown in FIG. 7. Indeed, in one embodiment, the side of the leg 274 had a shallow depression receiving the switch actuator button 117 with the drain reservoir 13 firmly pushed down in its vacuum charging position in the recesses 202 and 288 of the base unit 12. However, in the preferred embodiment shown in FIGS. 2, 6 and 7, the actuator 117 is depressed by a ramp 298 on the side of the leg 274 during insertion of the drain reservoir 13 in the base unit 12 and then simply bears frictionally on the leg 274, and a strap 299 fixedly depending from the right side of the cover 223 (FIGS. 1 and 2) buttons onto a pin 300 projecting from the right side of the base unit 12 (FIGS. 2 and 6) to help hold the bottom of the leg 274 firmly and sealingly against the annular vacuum seal member 292, so as to seal the vacuum port 278. In this way, with the tube 22 inserted in a closed wound W, the bottle 220 is evacuable to a subatmospheric pressure by means of the vacuum pump 31.

The drain reservoir 13 can be left in place in the base unit 12 in its FIG. 7 position. Alternatively, the thus "vacuum charged" drain reservoir can be forced upward with respect to the base unit 12 to unseat the switch actuator 117 from the detent 298 and thus permit the drain reservoir 13 to be lifted out of contact with the base unit 12. Thereafter, the drain reservoir 13, connected to the patient by means of the drain tube 22, can continue to draw drainage liquid from the wound W, and indeed can be moved with the patient to a location remote from the base unit 12, in the same general manner as in abovementioned U.S. application Ser. No. 404,791.

During evacuation of the drain reservoir 13 by the base unit 12, the hydrophobic filter unit 266 blocks movement of any liquid in the bottle 220 therepast into the hollow adapter 271, passage 262-264 and base unit 12. Similarly, with the drain reservoir 13 disconnected from the base unit 12, the hydrophobic filter 266 protects against entry of liquid from the bottle 220 therepast into the adapter 271 and passage 262-264 (to thereby prevent contamination of the vacuum pump system in the base unit 12 upon latter connection of the drain reservoir 13 to the base unit 12 for recharging the vacuum bottle 220). Thus, the hydrophobic filter unit 266 avoids the need for any sort of tilt responsive or fill responsive valve to close the passage 262-264 against drainage liquid. The hydrophobic filter unit 266 at any time permits removal of gases from the drain reservoir 13 by the base unit 12 to restore subatmospheric pressure in the bottle 220 (assuming that the bottle 220 is not filled with liquid), since the hydrophobic filter unit 266 will pass gases therethrough but not liquids.

The drain reservoir 13 installed on the base unit 12 is normally in its upright position shown in FIG. 2. However, when the drain reservoir 13 is separated from the base unit 12, it may be tipped or jiggled or otherwise moved to cause liquid within the bottle 220 to splash onto the surface of the hydrophobic filter unit 266.

To protect the hydrophobic filter 266 against coating with, and hence clogging by, lipids (the fat constituent in the body fluid being collected) a perforate baffle 302 of a nonpolar material is fixed in and extends across the interior of the bottle 220 to divide same into two separate chambers 303 and 304 (FIG. 2) at a location between the wound liquid inlet valve 249 and the hydrophobic filter 266. More particularly, the wound drain tube 22 and the emptying spout 228 communicate with the chamber 303 and the hydrophobic filter unit 266 communicates with the chamber 304.

In the embodiment shown, the baffle 302 is formed as a substantially rectangular panel extending the full height and thickness of the interior of the bottle 220. The baffle 302 can be of any convenient thickness but in the particular embodiment shown is in the range of $\frac{1}{4}$ to $\frac{5}{8}$ inch thick, for example $\frac{1}{2}$ inch thick. To maximize the area of the nonpolar material available for contact with fatty substances in the liquid within the bottle 220, the baffle 302 is preferably constructed of fibers randomly arranged in overlapping fashion, namely to form a fibrous mat wherein the fibers are held in place with respect to each other by a minimal amount of synthetic resin, preferably a nonpolar resin. Examples of suitable nonpolar materials include polypropylene, polyethylene and polystyrene. The resulting padlike baffle 302 is substantially shape-retaining and self-supporting. In the embodiment shown, baffle 302 is flexible enough to be bent or curved manually, but not sufficiently flexible as to be distorted by passage of wound drainage liquids therethrough in normal use.

It is contemplated that the baffle 302 may be otherwise made perforate to allow flow therethrough of wound drainage liquids and to have a high surface area for maximum attraction of lipids thereto, but the fibrous mat embodying the invention provides a low cost, readily available, and particularly effective form of perforate, high surface area baffle. One successful form of fibrous mat material for the baffle 302 is readily commercially available from Minnesota Mining & Manufacturing (3M) of Minneapolis, Minn. under the name "Superpolish Polyester" and marketed as manual polishing or scrubbing pads for household and industrial use.

Since polyester, polypropylene and polystyrene are successively more nonpolar, it is contemplated that a polypropylene and polystyrene baffle 302 may be even more effective than such polyester baffle.

The baffle 302 does not operate as a mechanical filter, that is, it does not operate by providing pores of a size to exclude large particles and pass small particles. Indeed, some of the components in the wound drainage liquid intended to be blocked by the baffle 302, namely lipids, may be physically smaller than other components, such as red blood cells, which need not be stopped by the baffle 302. Instead, the nonpolar material of the baffle 302 attracts lipids in the wound drainage liquid, since such lipids are nonpolar substances, so as to be attracted to other nonpolar substances.

The baffle 302 contains many through passages of small diameter, relatively great length and tortuous configuration. Thus, lipids attempting to pass through the baffle are forced to remain close to the surface of the nonpolar material of the baffle for a relatively long time to thereby increase the probability of being attracted to and trapped on the surface of the nonpolar material of the baffle. Also, maximizing the surface area of material exposed to the wound drainage liquid further maximizes the opportunity for lipids to be attracted to the material surface of the baffle. Accordingly, various components of the wound drainage liquid pass freely through the thickness of the baffle 302, namely the polar components therein which are not attracted by the nonpolar material of the baffle, while the nonpolar components of the liquid, namely lipids, tend to be entrapped by and stick to the material of the baffle.

In this way, the hydrophobic filter is protected by the baffle 302 against clogging by the lipids and fatty substances in the wound drainage liquid. This permits the use of a hydrophobic filter 266 which is particularly subject to clogging by the nonpolar components (lipids) of the wound drainage liquid, here for example a hydrophobic filter of PTFE material, which is also a nonpolar substance and hence attractive to lipids in the wound drainage liquid.

In the particular embodiment shown, the baffle 302 is held fixedly in position in the bottle 220 by ridges 308 molded into the inner surfaces of the front and rear walls and bottom wall of the bottle. The baffle 302 can be installed by sliding same down into the bottle 220 with its edges between the ridges 308 prior to installation of the cover 223 fixedly thereon.

OPERATION

Although the foregoing detailed description makes clear the operation of the device, such operation is summarized below for convenient reference.

With the remote end of the wound drainage tube 22 inserted in a closed wound W., as part of a surgical operation, and the drain receptacle 13 inserted down into the base unit 12, the switch member 117 and strap 298 hold the vacuum port 278 of the drain receptacle snugly against the seal 292 of the base unit 12 with the perforated head 296 in the recess 277 beneath the one-way valve 281. Engagement of the switch actuator 117 by the detent 298 compresses the switch actuator 117, turning on the switch 116 and enabling the control 16. Thus, when the vacuum transducer 294 in control unit 16 senses that the pressure in the bottle 220 is above a desired subatmospheric pressure range, for example at atmospheric pressure, it energizes the motor 32 of the vacuum pump 31 so that the vacuum pump 31 starts and lowers the pressure at the perforated head 296 and in the recess 277 of the drain reservoir 13. This reduced pressure opens the valve 281 to permit the vacuum pump to draw gases through the passage 262–264, the adapter 271 and the hydrophobic filter 266 from the interior of the bottle 220. The action of the control unit 16 may be like that described in abovementioned U.S. application Ser. No. 404,791.

The resulting subatmospheric pressure in the interior of the bottle 220, contrasted with the atmospheric pressure in the closed wound W, causes the drainage liquid from the wound W to flow through the drain line 22 and one-way valve 249 into the chamber 303 of the bottle 220.

The liquid drawn from the wound W will normally include blood as well as other material, such as lipids, released by surgical contact with tissue and bone. The wound drainage fluid can be considered as comprising blood as a solution with suspensions. The lipids are one of the components suspended in the blood. The blood is approximately 75% water. Water is a polar substance and thus one could say that the general characteristic of blood is that it is polar. In general, the solids in blood are polar because they are dissolvable in water with the polar components tending to be dissolvable in water. Nonpolar materials characteristically are not dissolvable in water. The baffle 302, as above stated, is nonpolar. The nonpolar components in the wound drainage liquid, before they can reach the hydrophobic filter 266, must come into contact with the material of the baffle 302. The nonpolar baffle material attracts the nonpolar material in the wound drainage liquid, namely the lipids. Thus, the nonpolar material in the wound drainage liquid, namely the lipids, are thus captured by the material of the baffle 302. Thus, the mainly polar components of the wound drainage liquid, which are free to pass through the baffle 302, are the only components which thus can enter the chamber 304, the lipids being excluded. Accordingly, the hydrophobic filter 266 may be contacted by liquids in the chamber 304, upon tilting or jiggling of the drain reservoir, or upon substantial filling thereof, but is protected from contact with nonpolar materials, particularly lipids. Thus, while the hydrophobic filter 266 may become wetted from time to time, it does not become coated and clogged. Hence, the hydrophobic filter tends to stay operative for its intended purpose of allowing evacuation of gas from the bottle 220 via vacuum pump 31 but preventing liquid flow therepast as would contaminate or disable the vacuum pump 31.

Were the hydrophobic filter 266 to become coated with a sufficient amount of fatty substance collected from the wound in the patient, the transducer 294 in the control unit 16 would thus shut off the vacuum pump 31 in the belief that an excessive vacuum existed in the drain reservoir 13, even if an insufficient vacuum existed in the drain reservoir. The drain reservoir 13 would therefore no longer properly vacuum drain the wound W and the system would be at that time nonoperative.

Depending on the character of the surgical operation and the lipid content in the drained liquid, and the agitation of the drain receptacle, if any, leading to coating of the hydrophobic filter 266, coating of the hydrophobic filter to the point of inoperativeness might occur in just a few hours (for example two or three hours). On the other hand, a given drain reservoir 13 may be required to drain a wound in a patient for, typically, 24 to 72 hours. Hence, in the absence of the baffle 302, the drain reservoir 13 may require, under certain circumstances, premature replacement. The baffle 302, on the other hand, has enabled use of a drain reservoir 13 and periodic recharging thereof with vacuum by a base unit 12 for the 24 to 72 hour periods typically required for patient support.

Once the drain reservoir 13 has been charged with vacuum by the base unit 12, and removed from the base unit, to allow more freedom in placement with respect to the patient and to allow movement of the patient, the subatmospheric pressure in the bottle 220 is maintained by the closed resilient cap 231 (which by being indented in its center indicates the presence of subatmospheric pressure in the bottle 220), and the closed umbrella valve 281.

Normally the drain receptacle 13 will be removed from the base unit 12 after the vacuum pump 31 has completed its lowering of the interior of the bottle 220 to subatmospheric pressure in the desired range and such vacuum pump 31 is turned off. Indeed, lifting of the drain receptacle 13 upward out of its engagement with the base unit 12 will shut off the vacuum pump 31 by deactuating the switch actuator 117, by in turn moving out of contact therewith the depending portion 274 of the drain reservoir 13.

The bottle 220 may eventually become filled, in which case the cap 231 is removed from the spout and liquid is poured out of the drain reservoir by tilting the bottle 220. Once that is done, the pressure is atmospheric in the bottle. Similarly, the bottle 220 may become partially filled with wound drainage liquid and at some time the pressure therein may approach atmospheric pressure whereupon the top portion 234 of the cap 231 pops up to indicate that charging of the drain reservoir with vacuum is required. Under either condition, the drain reservoir may be engaged with a conveniently located base unit 12 for recharging with subatmospheric pressure in the manner above described.

Once the drain reservoir 13 has performed its wound draining function, the drain tube 22 can be discarded but the base unit 12 can be used again for another patient and with other drain receptacles, without danger of contamination, because the hydrophobic filter 266 has prevented liquid in the drain reservoir 13 from reaching the base unit 12.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A continuous vacuum wound drainage system, comprising a base unit and a drain reservoir releasably secured to the base unit for partial evacuation to a subatmospheric pressure;
   wound connection means for connecting said drain reservoir to a wound and therewith for vacuum draining fluids from said wound;
   said base unit having a housing in turn having a forward facing groove which opens upward and is shaped and sized so that said drain reservoir is downwardly receivable in said groove, said base unit including control means and a power switch actuable for energizing said control means and a motorized vacuum pump actuable by said control means unit upon enabling of the latter by actuation of said power switch;
   said drain reservoir comprising a hollow upward opening bottle closed by a fixed cover, one end of said cover overhanging the side of said bottle;
   telescoping recess and leg means on said overhanging cover and the top of said base unit adjacent said groove, said telescoping recess and leg means being aligned substantially vertically for entering telescoped relation upon downward insertion of said drain reservoir into said groove in said base unit, said recess and leg means including an actuator for said power switch on said base unit and surface means on said cover overhanging end for actuating said power switch actuator in response to establishing of said telescoped condition of said recess and leg means due to insertion of said drainage receptacle and drain reservoir in said groove of said base unit.

2. The apparatus of claim 1 in which said recess and leg means comprises a leg depending from said overhanging end of said cover and spaced adjacent the side of said bottle, said recess and leg means further including a recess upwardly opening in the top of said base unit adjacent said groove, said switch actuator protruding into said recess, said surface means on said cover being a ramp surface on the side of said leg and engagable with said actuator for moving same upon downward insertion of said leg into said upward opening recess.

3. The apparatus of claim 1 in which said telescoping recess and leg means comprises a leg depending from the overhanging end of said cover and a recess upward opening in the top of said base unit adjacent said groove, vacuum passages leading from said vacuum pump to said recess and from the interior of said bottle through said cover and opening through said leg, a one way valve in the lower portion of said passage in said leg and oriented to normally close when the pressure outside the bottle is higher than that in the bottle and to open in response to a pressure at the lower end of said leg less than that in the bottle.

4. The apparatus of claim 3 including an enlarged diameter portion at the bottom of said passage in said leg, said valve being located to face downward at the top of said enlarged diameter portion, said valve having fixed portion and a resiliently flexible portion movable for opening and closing the valve, a head upstanding in said recess for reception into said enlarged diameter portion and into backing contact with the fixed portion of said valve with said leg fully seated in said recess.

5. The apparatus of claim 4 in which the lower end of said enlarged diameter portion of said passageway at the bottom of said leg is flared downwardly to ease reception of the head therein, said head carrying an annular seal engagable with the interior wall of the enlarged diameter portion of said passage at the bottom of said leg to effect a vacuum seal between the passages in said base unit and said drain reservoir.

6. A continuous vacuum wound drainage system, comprising a base unit and a drain reservoir releasably secured for partial evacuation to a subatmospheric pressure;
   wound connection means for connecting said drain reservoir to a wound and therewith for vacuum draining fluids from said wound;
   said base unit having a housing in turn having a forward facing groove which opens upward and is shaped and sized so that said drain reservoir is downwardly receivable in said groove, said base unit including control means and a power switch and a motorized vacuum pump actuable by said control unit upon enabling of the latter by actuation of said power switch;
   said drain reservoir comprising a hollow upward opening bottle closed by a fixed cover, one end of said cover overhanging the side of said bottle;
   telescoping recess and leg means on said overhanging cover and the top of said base unit adjacent said groove, said telescoping recess and leg means being aligned substantially vertically for entering telescoped relation upon downward insertion of said drain reservoir into said groove in said base unit, in which said base unit has a sidewardly facing recess, a battery pack arranged as a unit vertically slidable into and removable from said recess in said base unit, tongue-in-groove means on opposed walls of said recess and battery pack for guiding said battery pack into installed relation on said base unit and for preventing sideways movement of said battery pack out of said base unit, and electric contacts interposed between said base unit and battery pack for supplying current from said battery pack to said control means for energization of said vacuum pump, said base unit and drain reservoir having interconnectable vacuum passages in said telescoping recess and leg means and responsive to telescoping connection of the latter for enabling the vacuum pump to evacuate the drain reservoir.

7. A continuous vacuum wound drainage system, comprising:
   a base unit;
   a drain reservoir capable of being evacuated to a subatmospheric pressure;
   wound connection means for connecting said drain reservoir to a wound for vacuum draining fluids from said wound;
   said drain reservoir comprising an upward opening bottle closed by a fixed cover, one end of said cover overhanging the side of the bottle, telescoping recess and leg means on said overhanging cover and in the top of said base unit, said cover having an upward opening shallow recess having one end in the overhanging end of the cover and an opposite end overlying the top of the bottle and respectively communicating with vacuum passages extending downward into said telescoping recess and leg means and into said bottle, a plate-like closure covering said shallow recess and leaving a space above the bottom of said recess for passage of air from said bottle therethrough to said telescoping recess and leg means.

8. The apparatus of claim 7 in which said telescoping recess and leg means comprises a leg depending from said overhanging end of said cover of said drain reservoir and telescopically receivable down into an upward facing recess in the top of said base unit, said base unit having a vacuum passage communicating between said recess in said base unit and a vacuum source in said base unit, a means defining a one way valve in said depending leg, said one way valve being actuable for closing the end of said vacuum passage in said drain reservoir to preserve a subatmospheric pressure in said drain reservoir and being openable in response to application of a vacuum thereto from said base unit to evacuate said drain reservoir.

9. The apparatus of claim 7 including a hollow housing fixed to the underside of said cover within said bottle and communicating with said shallow recess in said cover, said housing having a hydrophobic filter associated therewith for permitting air to be drawn from said bottle into said shallow recess but preventing liquid from passing therethrough.

10. The apparatus of claim 7 including an empty spout on said cover spaced rom said shallow recess and communicating with the bottle interior, a cap releasably located on said spout for closing same against air leakage into said bottle and removable therefrom to allow emptying of liquid from said bottle through said spout, said wound connecting means being located on said cover intermediate said shallow recess and spout, said spout being located adjacent the end of the cover remote from said telescoping recess and leg means.

11. The apparatus of claim 10 in which said cap is resilient and has a portion distortable by a pressure drop thereacross to indicate a subatmospheric pressure in said bottle.

12. The apparatus of claim 10 in which the cover has a second end overhanging said bottle and a strap depending from said second end and engagable with means on a adjacent side of said base unit for assisting holding of the drain reservoir in position on the base unit, said telescoping recess and leg means also having means frictionally assisting in holding said drain reservoir in place on said base unit.

* * * * *

UNITED STATES PATENT AND TRADEMARK OFFICE
CERTIFICATE OF CORRECTION

PATENT NO. : 4,826,494

DATED : May 2, 1989

INVENTOR(S) : William M. Booth III et al.

It is certified that error appears in the above-identified patent and that said Letters Patent is hereby corrected as shown below:

Col. 9, lines 22 & 23; change "control means unit upon enabling of the latter by actuation of said power switch" to ---control means---.

Col. 9, lines 38 & 39; change "said drainage receptacle and drain" to ---said drain---.

Col. 12, lines 3 & 4; change "an empty spout" to ---an emptying spout---.

Col. 12, line 4; change "spaced rom said" to ---spaced from said---.

Signed and Sealed this

Twenty-eighth Day of November 1989

Attest:

JEFFREY M. SAMUELS

*Attesting Officer*    Acting Commissioner of Patents and Trademarks